(12) United States Patent
Gammons et al.

(10) Patent No.: US 6,224,543 B1
(45) Date of Patent: May 1, 2001

(54) NON-LATEX INVERTED SHEATH DEVICE

(75) Inventors: Clifford Eugene Gammons, Loudon; Joseph G. Jones, Englewood, both of TN (US)

(73) Assignee: Adroit Medical Systems, Inc., Loudon, TN (US)

( * ) Notice: Subject to any disclaimer, the term of this patent is extended or adjusted under 35 U.S.C. 154(b) by 0 days.

(21) Appl. No.: 09/228,830

(22) Filed: Jan. 12, 1999

Related U.S. Application Data

(63) Continuation-in-part of application No. 09/083,234, filed on May 21, 1998, now abandoned.

(51) Int. Cl.⁷ .............................. A61B 1/00; B32B 1/08
(52) U.S. Cl. .................. 600/124; 428/35.2; 206/306
(58) Field of Search .................... 600/121, 122, 600/123, 124, 125; 606/1; 206/306, 363; 604/171, 197; 374/158; 428/35.2, 35.5

(56) References Cited

U.S. PATENT DOCUMENTS

| | | | |
|---|---|---|---|
| 3,308,940 | * 3/1967 | Morris, Jr. | 206/306 |
| 3,809,230 | * 5/1974 | Poncy | 206/306 |
| 3,847,280 | * 11/1974 | Poncy | 206/306 |
| 4,062,239 | 12/1977 | Fowler et al. . | |
| 4,164,285 | * 8/1979 | Dorman | 206/306 |
| 4,165,000 | 8/1979 | Poncy . | |
| 4,197,944 | 4/1980 | Catlin . | |
| 4,241,828 | * 12/1980 | Bourdelle et al. | 206/306 |
| 4,614,442 | 9/1986 | Poncy . | |
| 4,684,018 | 8/1987 | Jarund . | |
| 4,757,381 | * 7/1988 | Cooper et al. | 348/66 |
| 4,823,949 | 4/1989 | Bala . | |
| 5,069,337 | 12/1991 | Bala . | |
| 5,667,068 | * 9/1997 | Weaver | 206/363 |
| 5,769,224 | * 6/1998 | Poncy et al. | 206/365 |
| 5,795,632 | * 8/1998 | Buchalter | 428/35.2 |

\* cited by examiner

*Primary Examiner*—John P. Leubecker
(74) *Attorney, Agent, or Firm*—Pitts & Brittian

(57) ABSTRACT

An device for covering an elongated medical probe such as a vaginal, rectal, ultra sound or the like type probe. In the preferred embodiment the sheath is tubular and includes a nose and an open end through which the medical probe is inserted. Preferably the sheath is packaged by mounting it on a flexible carrier in a partially elongated position. An adhesive material releasably secures the sheath to the carrier such that the nose of the sheath is inverted and defines a folded nose opening to facilitate positioning the sheath over the tip of a conventional medical probe.

9 Claims, 4 Drawing Sheets

NON-LATEX INVERTED SHEATH DEVICE

This application is a C.I.P. of Ser. No. 09/083,234, filed on May 21, 1998, now abandoned.

TECHNICAL FIELD

This invention relates to sheaths for medical probes and more particularly concerns such a sheath which is releasably mounted on a carrier in an inverted nose position to facilitate movement of the sheath onto the tip of a medical probe prior to the insertion of the probe into the body of a patient.

BACKGROUND ART

Modern medical practices require the application of a sheath to the tip of conventional medical probes, such as ultra sound, rectal or vaginal probes, prior to insertion of such probes into the body of a patient. Moreover, investigatory medical probes are often used to penetrate the body through a wound to discern the healing status of open tissue. Such medical practices normally require utilization of a non-latex sheath since the sheath may contact blood or other body fluids in which latex has been found to cause infection or an allergic reaction.

Application of the sheath to the probe is normally preceded by injection of a suitable moisturizing gel into the nose of the sheath. This gel further enhances the optical or ultra sound coupling between the active end of the probe tip and the sheath to enhance the quality of medical data gathered upon insertion into the body.

Prior art devices have normally involved the mounting of a fully extended sheath onto a carrier. In order to extend the probe into the entire length of the sheath, the medical technician or doctor will insert the probe through the sheath opening and slowly manipulate the tip of the probe such that it travels through the sheath length to its nose. This process can result in inadvertent contact with the wall of the sheath which will engage or become in direct contact with the patient. Moreover, it is difficult to inject the transmission gel into the nose of a fully extended sheath since such gel must travel the entire length of the sheath to be deposited proximate the subsequent placement of the active end of the probe tip.

Typical prior art devices are disclosed in the following U.S. Patents:

| U.S. Pat. No. | Inventor(s) | Issue Date |
| --- | --- | --- |
| 4,062,239 | C. F. Fowler, et al. | Dec 13, 1977 |
| 4,165,000 | G. W. Poncy | Aug. 21, 1979 |
| 4,197,944 | D. G. Catlin | Apr. 15, 1980 |
| 4,614,442 | G. W. Poncy | Sept. 30, 1986 |
| 4,684,018 | E. Järund | Aug. 4, 1987 |
| 4,823,949 | H. Bala | Apr. 25, 1989 |
| 5,069,337 | H. Bala | Dec. 3, 1991 |

Of these devices, that disclosed by Fowler, et al. ('239) is a probe cover incorporating an inner sheath with a probe end engagement section which defines a reduced width at the distal end thereof. The reduced width is formed by a non-permanent bonding of the sheath layers using a graduated strength bond.

Poncy ('000) discloses a sterile sheath carried on a substrate having a tear tab. Poncy does not disclose an inverted portion of the sheath. The sheathes disclosed by Bala ('337 and '949), Järund ('018) and Poncy ('442) are similar in constriction to the '000 device.

The '944 device disclosed by Catlin is defined by two sheaths disposed in an end to end fashion, with the probe being inserted into a smaller of the two, and the larger of the two then being inverted over the first. The probe is thus disposed within two sheathes once completely inserted.

Accordingly, it is an object of the present invention to provide a tubular sheath having an inverted nose releasably mounted on a carrier such that the tip of a probe can be readily inserted into the nose as the balance of the length of the sheath is moved about the probe length. Another object of the present invention is to provide such a sheath with an inverted nose that shields the surface of the sheath wall which contacts the patient upon insertion of the probe into the patient's body, such that inadvertent contact with this sheath surface on the patient side is reduced as the sheath is placed over the medical probe.

Other objects and advantages of the invention over the prior art will become apparent to those skilled in the art upon reading the detailed description together with the drawings which are described below.

DISCLOSURE OF THE INVENTION

In accordance with various features of this invention, an improved tubular sheath is provided which can be readily mounted upon a medical probe in a manner which assists in enhancing the sterility of the surface of the sheath that will ultimately contact the body of a patient. In the preferred embodiment, the sheath is tubular and has an open end and a nose into which the medical probe is inserted. The sheath is mounted in a partially elongated disposition on a flexible carrier. An adhesive material serves to releasably secure the sheath to the carrier such that the nose of the sheath is inverted and defines a folded nose opening which facilitates receiving a transmission gel and the active tip of the probe as it is being folded along the length thereof during application of the sheath to the probe.

BRIEF DESCRIPTION OF THE DRAWINGS

The above mentioned features of the present invention will become more fully understood from the following detailed description of the invention read together with the drawings in which.

BEST MODE FOR CARING OUT THE INVENTION

Figure 1:
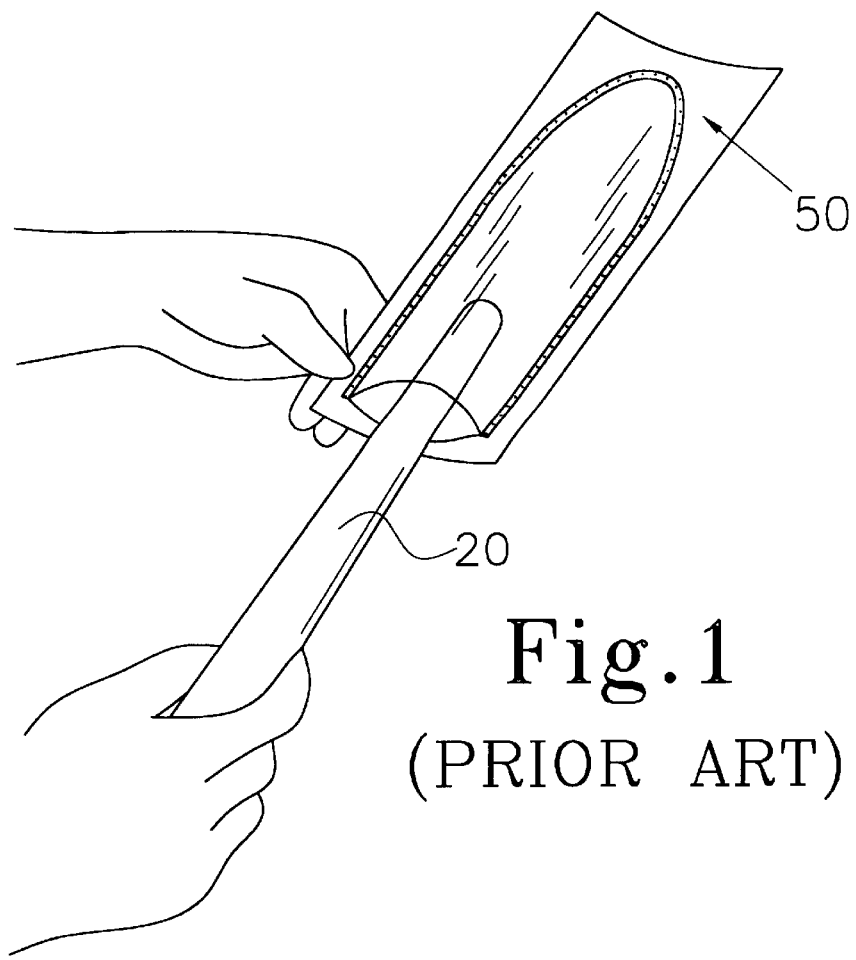
FIG. 1 illustrates a typical prior art medical probe sheath mounted on a carrier in a substantially fully extended disposition requiring insertion of the probe along the entire length of the sheath as it is disposed on the carrier.

An improved device for covering an elongated medical probe, such as an ultra sound, rectal or vaginal probe, constructed in accordance with various features of the present invention is illustrated generally at 10 in FIG. 1. This device 10 comprises a tubular sheath 12 having an open end 14 and a nose 16 into which the tip 18 of a medical probe 20 is inserted. This sheath 12 is preferably fabricated from a non-latex material such as poly-ether urethane or another suitable hybrid plastic such as metalacine. Medical applications involving direct contact with the interior of the body or blood require the utilization of a non-latex sheath, as a general rule, since it has been found that latex may cause an allergic reaction. Moreover, it has been found that infections can result in the event latex materials contact open tissue or other bleeding body parts.

Figure 2:
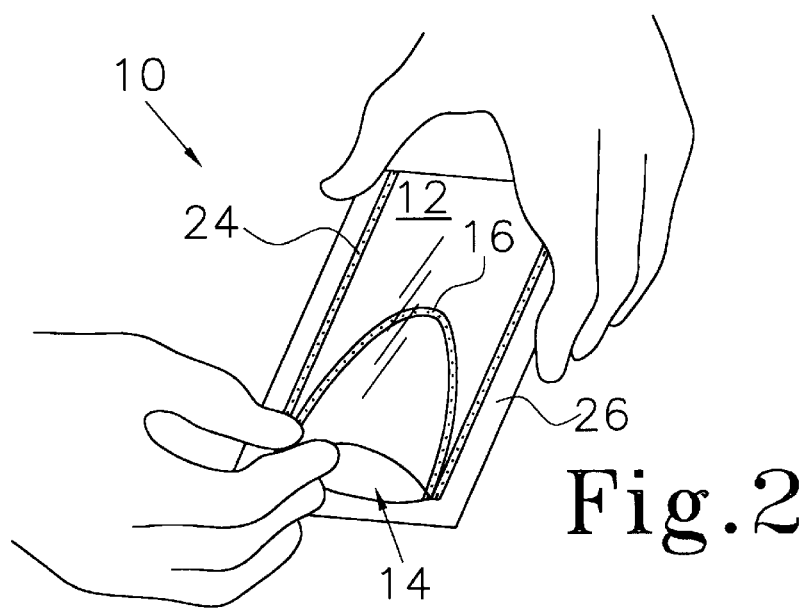
FIG. 2 illustrates a tubular sheath constructed in accordance with various features of the present invention having an inverted nose defining a nose opening through which the tip of the probe is inserted as it is folded along the length thereof.
Figure 3:
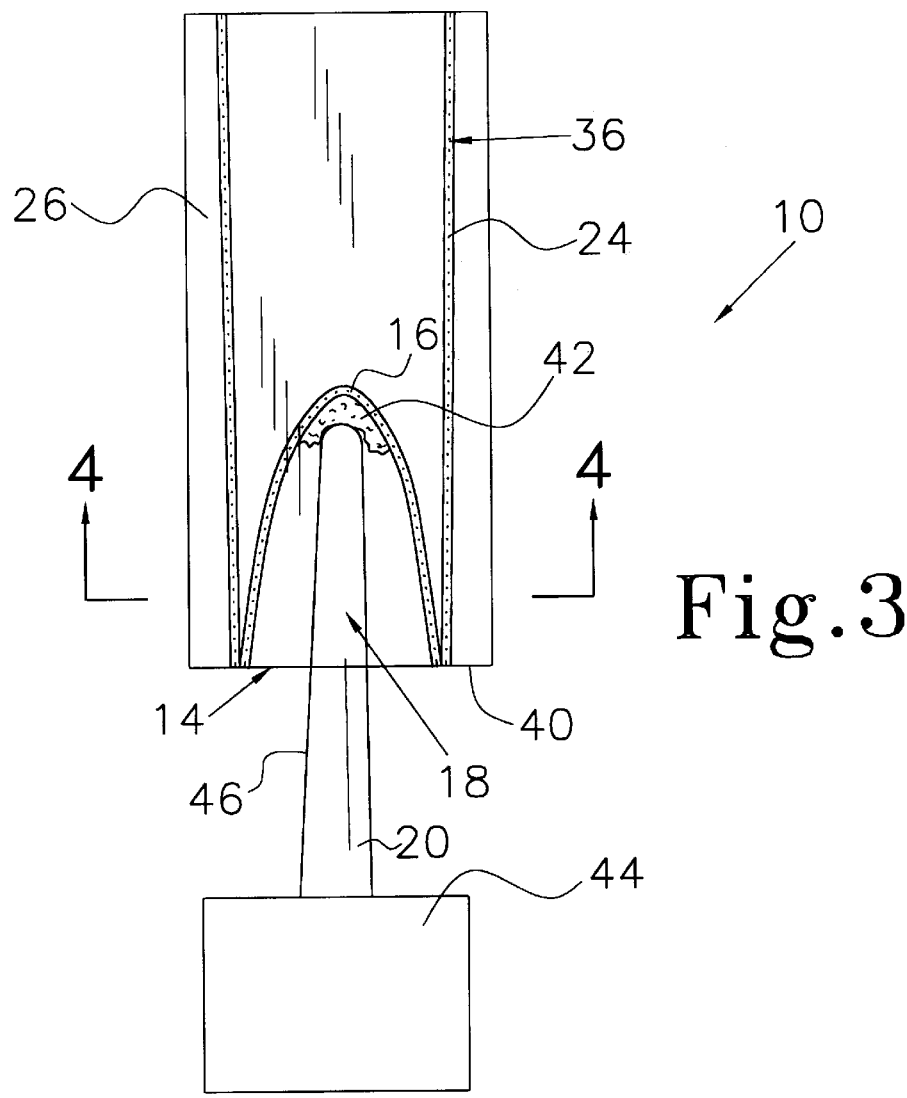
FIG. 3 is a plan view of a sheath depicting the welds used in forming the sheath configuration.
Figure 7:
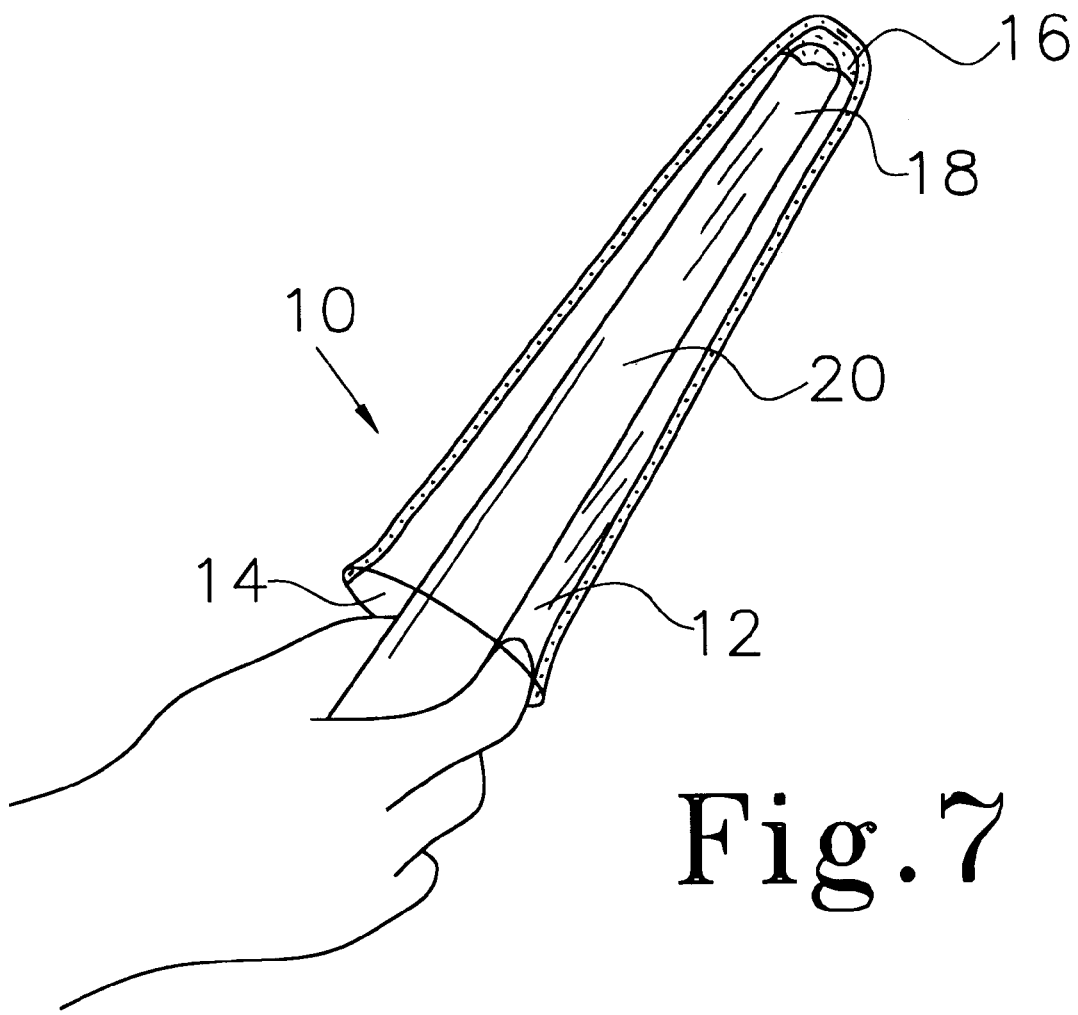
FIG. 7 depicts a sheath constructed in accordance with the various features of the present invention which has been fully mounted along the length of a medical probe.

In the embodiment illustrated in FIGS. 3 and 7, it will be noted that the sheath configuration is tapered to facilitate insertion of the probe 20 into the sheath 12. In certain applications, it may be desirable that the sheath 12 has parallel welds 24 as is shown in FIG. 2. Moreover, the sheaths can be fabricated in various lengths such as nine inches, twelve inches and in certain applications where a probe is used for investigating the intestines, the sheaths may be in excess of 72 inches.

The sheath 12 is mounted on a carrier 26 in the preferred embodiment as is shown in the FIGS. 2–6. This carrier 26 is preferably flexible and elongated to releasably receive the sheath thereon. In the preferred embodiment, the tubular sheath 12 is fabricated from two sheets 30 and 32 of a non-latex material. The thickness of the sheath sheets is selected to provide the desired flexibility for ready application to the medical probe 20. In the preferred embodiment the sheet material has a thickness of one-half mil (0.005 inches) to five mils (0.005 inches).

Figure 4:
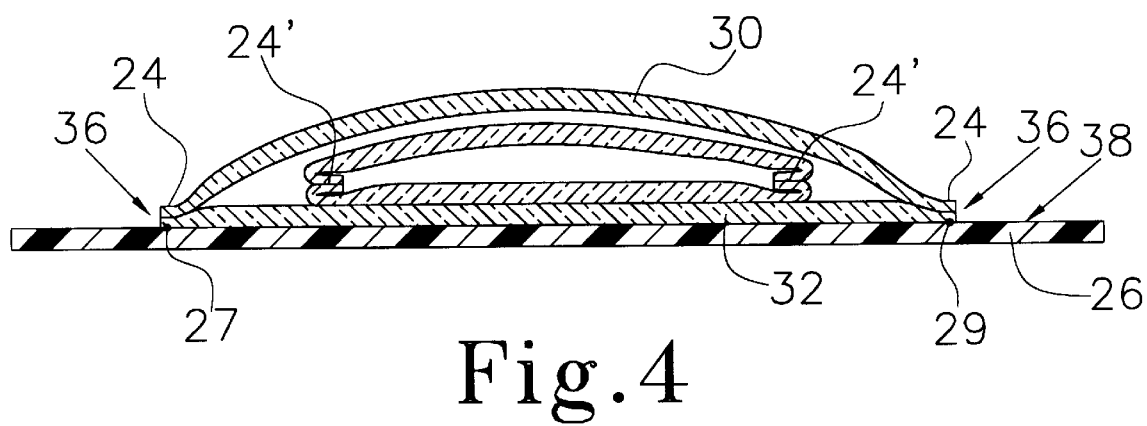
FIG. 4 is a sectional view taken along line 4—4 in FIG. 3 which depicts the welding of the sheath edges to the carrier and the position of the inverted nose mounted on the carrier in a partially extended position.

During fabrication of the sheath 12 from the sheets 30 and 32, the perimeter 36 of the sheath is welded such that the individual edges of the sheets are juxtaposed and sealed as is shown in FIGS. 3 and 4. At the same time the sheath is fabricated by sealing the edges, the excess material is trimmed in the preferred embodiment and the sheath is secured to the carrier 26 by the formation of welds at the locations 27 and 29 shown in FIG. 4. These welds that secure the sheath 12 to the carrier 26 comprise slightly melted sheath material which further serves to releasably heat seal the sheath to the carrier. To this end, the carrier 26 preferably is provided with a gloss finish on the surface 38 (see FIG. 4) to which the sheath is secured. It has been found that securement of the sheath to the carrier in this manner serves to provide a suitable and releasable seal such that the probe can be readily inserted into the sheath as is shown in FIGS. 5 and 6.

It is desirable for the nose 16 of the sheath to be positioned proximate the edge 40 of the carrier 26 to facilitate placement of the probe tip into the sheath. By placement of the nose at this location on the carrier as is illustrated in FIG. 3, a user can first insert a transmission gel 42 into the inner portion of the sheath such that it is contained in the nose. With the nose displaced proximate the edge 40 of the carrier, insertion of such gel 42 from a gel applicator 44 through the applicator nozzle 46 can readily be accomplished. In prior art devices such as shown in FIG. 1 at 50, it will be recognized that it is difficult to place the gel into the nose of the sheath inasmuch as the application requires movement of the gel along the entire sheath length.

After the gel is placed in the nose of the sheath, the probe 20 is then inserted into the nose opening 52 formed by the fold resulting upon inverting the nose into the tubular sheath 14. It will be noted that the outside surface of the sheath 14 which contacts the body upon insertion of the sheath covered probe therein, is partially folded into the sheath such that this surface contacts a selected length of the inside surface of the sheath. In this manner, the folded nose opening 52 is defined for readily receiving the tip of the probe at a location remote from the opening 14 of the sheath. After the tip of the probe is inserted into the nose as is shown in FIG. 5, the probe is pushed forward in the direction of the arrow 56. As this is accomplished, the releasably secured sheath 14 peels from the carrier 26 as illustrated in FIG. 6 until the probe is covered by the full sheath length which is illustrated in FIG. 7. At this point, it will also be noted that the sheath has been separated from the carrier which can now be discarded.

Figure 5:
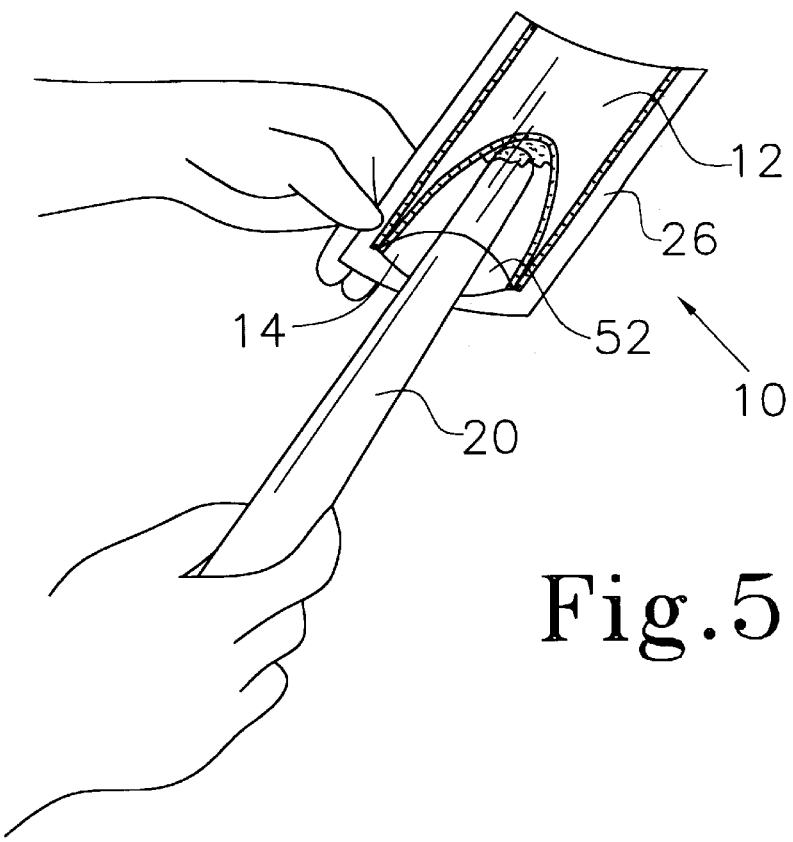
FIGS. 5 and 6 disclose the displacement of the tubular sheath on a carrier as the probe is inserted into the sheath in a manner which assists in preventing inadvertent human contact with the surface of the sheath that will contact the body upon insertion of the sheath covered probe.
Figure 6:
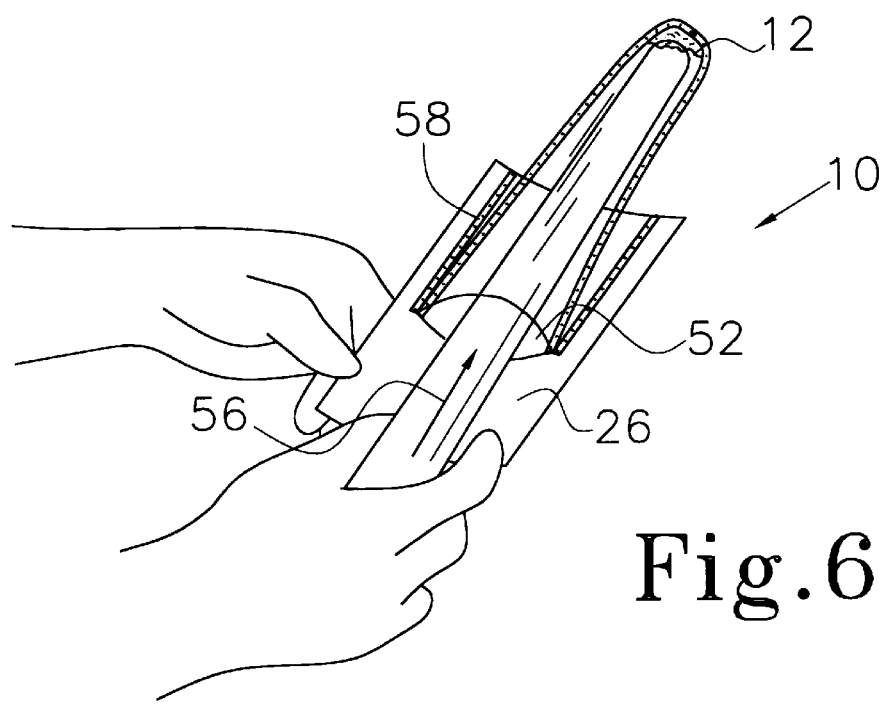

As will be noted in FIGS. 5 and 6, the outside surface of the sheath which contacts the body is partially folded into the sheath such that this outside surface of the sheath contacts the selected length of the outside surface of the sheath spaced from the nose. This is illustrated at the location 58 of FIG. 6. In this manner, the outside surface of the sheath is shielded from inadvertent human contact such that when the sheath is mounted onto the probe as shown in FIGS. 5–7, this outside sheath surface has never been contacted by human hands. This prevents the inadvertent contamination of this outside surface prior to the time it is inserted into the body of a patient.

It will also be noted in FIGS. 5 and 6 that as the probe is inserted into the sheath in the direction of the arrow 56, the nose opening 52 moves along the length of the carrier in the direction of the arrow 56 as the sheath is folded about the nose opening onto the probe 20. The inverted nose position of a sheath is further shown in FIG. 4 in the sectional view taken along line 4—4 of FIG. 3.

From the foregoing description, it will be recognized by those skilled in the art that an improved device for covering an elongated medical probe having certain advantages of the known prior art has been provided. More specifically, the device of the present invention includes an elongated tubular sheath having an inverted nose releasably mounted onto a flexible carrier. The nose is positioned at a convenient location such that transmission gel can be readily inserted therein. Moreover, this convenient positioning of the nose allows for ready receipt of the probe therein such that the probe can then be advanced in the direction of the arrow 56 as the sheath is removed from the carrier simultaneously with the application of the sheath to the probe. In this manner, the outside surface of the sheath wall which will ultimately engage the body of the patient through an open wound or other orifice is shielded until the sheath is applied to the probe thus assisting to prevent inadvertent contact with this outside surface.

While a preferred embodiment has been shown and described it will be understood that it is not intended to limit the invention, but rather it is intended to cover all modifications and alternate methods falling within the spirit and the scope of the invention as defined in the appended claims.

Having thus described the aforementioned invention,

I claim:

1. A device for covering an elongated medical probe including:

a tubular sheath having an open end and a nose adapted to receive the tip of said medical probe, said open end defining an open configuration prior to insertion of said medical probe into said nose of said tubular sheath, said tubular sheath defining an elongated configuration and being fabricated from two sheets of non-latex material bound together with a continuous weld about a portion of a perimeter of said tubular sheath, said weld terminating at opposite sides of and defining said open end, said nose of said sheath being inverted to define a nose opening to facilitate receiving the tip of said medical probe; and a flexible carrier for receiving said sheath in a partial elongated position, said sheath being releasably securable to said carrier, said sheath being removed from said flexible carrier upon inversion of said sheath by said medical probe.

2. The device of claim 1 wherein said tubular sheath is fabricated from poly-ether urethane.

3. The device of claim 1 wherein said tubular sheath is fabricated from a hybrid plastic.

4. The device of claim 1 wherein said tubular sheath is fabricated from metalacine plastic.

5. The device of claim 1 wherein said flexible carrier is fabricated from paper stock having a gloss finish.

6. The device of claim 1 wherein said sheath is releasably secured to said carrier by welding along at least a portion of said perimeter of said sheath during formation of said continuous weld of said two sheets of non-latex material.

7. A device for covering an elongated medical probe including:

a tubular sheath fabricated from poly-ether urethane having an open end and a nose adapted to receive the tip of said medical probe, said open end defining an open configuration prior to insertion of said medical probe into said nose of said tubular sheath, said tubular sheath defining an elongated configuration and being fabricated from two sheets of non-latex material bound together with a continuous weld about a portion of a perimeter of said tubular sheath, said weld terminating at opposite sides of and defining said open end, said nose having an inverted configuration formed by folding said sheath nose such that an outside surface of said sheath is partially folded into said sheath to define an opening for readily receiving the tip of said medical probe as said sheath is received thereon; and a flexible carrier for receiving said sheath in a partially elongated position, said sheath being releasably securable to said flexible carrier, said sheath being removed from said flexible carrier upon inversion of said sheath by said medical probe.

8. The device of claim 7 wherein said flexible carrier is fabricated from paper stock having a gloss finish.

9. The device of claim 7 wherein said tubular sheath is releasably secured to said carrier by welding along at least a portion of said tubular sheath perimeter during fabrication of said tubular sheath.

* * * * *